(12) United States Patent
Erlen et al.

(10) Patent No.: US 12,728,195 B2
(45) Date of Patent: Sep. 8, 2026

(54) DEVICE FOR ADMINISTERING MEDICAL LIQUID, HAVING A HEAT SINK WITH COOLING FINS

(71) Applicant: B. Braun Melsungen AG, Melsungen (DE)

(72) Inventors: Christoph Erlen, Kassel (DE); Gerhard Schoeffel, Blaustein (DE); Joachim Schuetz, Fulda (DE); Daniel Wolf, Bibertal (DE)

(73) Assignee: B. Braun Melsungen AG, Melsungen (DE)

( * ) Notice: Subject to any disclaimer, the term of this patent is extended or adjusted under 35 U.S.C. 154(b) by 275 days.

(21) Appl. No.: 17/928,332

(22) PCT Filed: Feb. 22, 2022

(86) PCT No.: PCT/EP2022/054345
§ 371 (c)(1),
(2) Date: Nov. 29, 2022

(87) PCT Pub. No.: WO2022/180013
PCT Pub. Date: Sep. 1, 2022

(65) Prior Publication Data

US 2023/0390482 A1 Dec. 7, 2023

(30) Foreign Application Priority Data

Feb. 24, 2021 (DE) ..................... 10 2021 104 413.8

(51) Int. Cl.

| | |
|---|---|
| ***A61M 5/14*** | (2006.01) |
| ***A61M 5/145*** | (2006.01) |
| ***H05K 7/20*** | (2006.01) |

(52) U.S. Cl.
CPC ........ *A61M 5/1415* (2013.01); *A61M 5/1452* (2013.01); *H05K 7/20418* (2013.01); *A61M 2205/3606* (2013.01)

(58) Field of Classification Search
CPC .. A61M 5/1415; A61M 5/1456; A61M 5/142; A61M 5/1452; A61M 2205/3606;
(Continued)

(56) References Cited

U.S. PATENT DOCUMENTS 3,187,812 A * 6/1965 Staver ................. H01L 23/3672 257/713
4,964,785 A 10/1990 Schoenwald et al.
(Continued)

FOREIGN PATENT DOCUMENTS

CN 107426942 A 12/2017
CN 11584989 A 8/2020
(Continued)

OTHER PUBLICATIONS

Search Report received in German Application No. 10 2021 104 413.8 dated Dec. 6, 2021, with translation, 12 pages.
(Continued)

*Primary Examiner* — Cris L. Rodriguez
(74) *Attorney, Agent, or Firm* — Christopher A. Rothe; CM Law

(57) ABSTRACT

A device for administering medical liquid, in particular an infusion pump, and a system that includes the device and a holding device. The device includes a housing and a component that generates heat during use of the device. The component is arranged inside the housing. A passive heat sink is attached to an outer side of the housing and is connected thermally, in particular in a heat-conducting manner, to the component. The heat sink has cooling fins.

14 Claims, 2 Drawing Sheets

(58) Field of Classification Search
CPC .. H05K 7/20; H05K 7/20436; H05K 7/20418; H05K 7/20154; F21V 29/2212; H01C 1/084
USPC .......................................................... 361/709
See application file for complete search history.

(56) References Cited

U.S. PATENT DOCUMENTS

| | | | | |
|---|---|---|---|---|
| 5,133,650 | A * | 7/1992 | Sunderland ....... | A61M 5/14232 417/477.2 |
| 6,068,051 | A * | 5/2000 | Wendt ................. | H01L 23/3675 361/720 |
| 6,385,047 | B1 * | 5/2002 | McCullough ......... | H01L 23/467 257/722 |
| 9,402,939 | B2 * | 8/2016 | Visconti ........... | A61B 17/00234 |
| 10,034,975 | B2 | 7/2018 | McLennan et al. | |
| 11,084,925 | B2 * | 8/2021 | Kim ........................ | F21V 29/74 |
| 2002/0041487 | A1 | 4/2002 | McCullough et al. | |
| 2007/0233003 | A1 | 10/2007 | Radgowski et al. | |
| 2013/0281965 | A1 | 10/2013 | Kamen et al. | |
| 2017/0296745 | A1 | 10/2017 | Kamen et al. | |

FOREIGN PATENT DOCUMENTS

| | | | | |
|---|---|---|---|---|
| EP | 1843476 | A1 | 10/2007 | |
| EP | 3696908 | A1 | 8/2020 | |
| WO | WO-2020123681 | A1 * | 6/2020 | ............. G11C 29/06 |

OTHER PUBLICATIONS

Search Report received in International Application No. PCT/EP2022/054345 dated Jul. 19, 2022, with translation, 5 pages.

Written Opinion received in International pages Application No. PCT/EP2022/054345 dated Jul. 19, 2022, with translation, 12 pages.

Examination Report received in European Application No. 22 708 883.8-1122 dated Dec. 9, 2022, with translation, 6 pages.

Office Action received in Chinese Application No. 202280003618.6 dated Apr. 30, 2026, with translation, 8 pages.

Search Report received in Chinese Application No. 202280003618.6 dated Apr. 27, 2026, with translation, 6 pages.

* cited by examiner

DEVICE FOR ADMINISTERING MEDICAL LIQUID, HAVING A HEAT SINK WITH COOLING FINS

CROSS-REFERENCE TO RELATED APPLICATIONS

This application is the United States national stage entry of International Application No. PCT/EP2022/054345, filed Feb. 22, 2022, and claims priority to German Application No. 10 2021 104 413.8, filed Feb. 24, 2021.

FIELD

The present disclosure relates to a device for administering medical fluid, in particular an infusion pump. Furthermore, the present disclosure relates to a system comprising a holding device, such as a stand, and such a device.

BACKGROUND

Infusion pumps are basically differentiated between syringe pumps and hose pumps. In syringe pumps, a syringe filled with the fluid to be administered is moved by a drive so that a syringe plunger of the syringe is moved at a controlled feed rate in order to convey the fluid out of the syringe. In the case of hose pumps, a hose filled with the fluid to be administered is moved by a drive, for example via a peristaltic system, in order to convey the fluid out of the hose.

Such infusion pumps have a plurality of (electronic) components whose operation generates heat. Such an infusion pump is known, for example, from U.S. Pat. No. 10,034,975 B2, which has an infusion pump with a housing and a heat-generating component arranged therein.

The generated heat has to be dissipated to the environment in order to keep the temperature of the infusion pump within an acceptable range for all components and to protect the components from overheating. For this purpose, known infusion pumps have a fan/ventilator installed in the infusion pump housing to dissipate the heat via air cooling by blowing air flowing along the surfaces of the heat-generating (electronic) components out of the infusion pump housing. However, the disadvantage of this is that openings have to be provided in the infusion pump housing for guiding the air to the outside. Fluids or other undesirable external influences can in turn enter the infusion pump housing through these openings, which must be avoided to ensure the functionality of the infusion pump. A further disadvantage is that the fan and any cooling generator, provided if necessary, used to cool the air have to be supplied with electrical power, so that cooling may fail if there is no power supply. In addition, the fan and the cooling generator require additional installation space within the infusion pump housing. Due to the compact design of the infusion pump and its limited battery capacity, such air cooling of the (electronic) components is therefore not practical.

SUMMARY

It is therefore an object of the present disclosure to provide a device for administering medical fluid, in particular an infusion pump, in which it can be ensured at all times that the temperature within the device does not exceed a permissible maximum temperature of all components contained in the device. At the same time, the device is intended to have a compact design, to be easy to clean and/or to sterilize, and to protect the components arranged within a device housing from external influences in order to ensure functionality. It is also the object of the present disclosure to provide a system comprising such a device and a holding device for holding the device.

In particular, the device for the administration of medical fluid is configured as an infusion pump. For example, the device may be configured as a syringe pump or a hose pump.

The device has a housing and at least one heat-generating component, i.e. a component to be cooled, in particular when the device is in use. The component is arranged within the housing. For example, the component may be configured as an electronic component. Also, the device may have several such heat-generating components at least during use of the device. In an infusion pump, the heat-generating components may include, for example, a power adaptor for supplying power to other electrically operated components and/or an accumulator for supplying power to other electrically operated components. In addition, a radio module, such as a WLAN-/WIFI-module or a Bluetooth module, for signal transmission may be a heat-generating component. An electromotive component, in particular a drive for conveying the fluid, may also be a heat-generating component. Heat-generating components, in particular of an infusion pump, may also include, for example, a display unit for displaying data relevant to operation, a control device for controlling the device, for example the display unit or the drive, or the like. In other words, heat is generated inside the housing of the device, which has to be dissipated from the housing.

According to the present disclosure, the device comprises a passive heat sink/cooling element mounted on an outer side of the housing. A passive heat sink is understood to be a component that releases heat to the environment via passive cooling. By attaching the heat sink to the outside of the housing, the heat sink can dissipate heat directly to the environment. Here, passive cooling is the cooling of machines, of electrical and electronic devices and components solely on the basis of free/natural convection and heat radiation, where the waste heat is released or radiated into the surrounding air. In contrast, active cooling uses a fan or pump to remove the heat energy from the component to be cooled. The advantage of passive cooling over active cooling is primarily that no electrical energy is required for cooling.

According to the present disclosure, the heat sink is thermally connected to the component, in particular in a heat-conducting manner. This means, therefore, that heat is transported by heat conduction from the interior of the housing to the heat sink on the outside to be released to the environment. In other words, a different type of a heat transport process, namely heat conduction by mechanical contact, is specifically used for heat transfer inside the housing than for heat transfer outside the housing, which is convection and/or heat radiation. Thus, in contrast to the prior art, convection within the housing forced by a fan is no longer used to dissipate heat by entrainment in the air conveyed to the outside. This has the advantage that openings no longer have to be provided in the housing to allow the air to be conveyed out, since the heat is transferred to the outside of the device by direct mechanical contact. This also prevents undesirable media from entering the housing through the openings, so that the cleanability and sterilizability of the device can be significantly increased. Another decisive advantage is that no electrical energy has to be used to drive such a fan, so that cooling of the component/s is independent of the power supply or battery capacity and thus fail-safe.

According to the present disclosure, the heat sink has cooling ribs/cooling fins. By providing the cooling ribs, the surface area of the heat sink can be increased and thus the heat transfer to the cooling can be improved.

According to a preferred embodiment, the device may comprise a heat-conducting profile arranged within the housing, such as a heat-conducting sheet or the like. The heat-conducting profile may be thermally connected, preferably directly, i.e. with mechanical contact, to the component generating heat/the component to be cooled. The heat-conducting profile may be thermally connected, preferably directly, i.e. with mechanical contact, to the heat sink. Due to the heat-conducting, preferably direct, connection through the heat-conducting profile, the heat of the component is transported to the outside in a suitable and simple manner. In particular, the heat-conducting profile may be connected to the component and/or the heat sink in a surface-to-surface contact/contact in a close-fit manner. The transferable heat capacity can be increased by the surface-to-surface contact and the resulting contact surface. Preferably, the heat-conducting profile may be made from a material whose heat conductivity is greater than 10 W/mK, preferably greater than 50 W/mK, more preferably greater than 100 W/mK. In particular, the heat-conducting profile may be made from a metal, for example aluminum or copper, or alternatively from a ceramic material, in particular an engineering ceramic, such as aluminum oxide or aluminum nitride.

According to a further development of the preferred embodiment, the heat sink may have a preferably planar contact surface that rests/abuts against a preferably planar contact surface of the heat-conducting profile or is connected to a preferably planar contact surface of the heat-conducting profile via a thermal layer, such as a thermal paste. The heat sink may, for example, be arranged to penetrate a recess in the housing. This has the advantage that thermal resistance of the housing material is bypassed.

According to a further development of the preferred embodiment, the heat-conducting profile may thermally connect several heat-generating components to the heat sink. This has the advantage that the number of components is kept as low as possible if a heat-conducting profile can function for the heat dissipation of several components. Preferably, the multiple components may be arranged adjacent to each other. This means that the heat-conducting profile can be configured to be as short as possible so that the heat only has to be dissipated over a shorter distance.

According to a further development of the preferred embodiment, the heat-conducting profile may be arranged at a distance from the housing. This means that the heat-conducting profile preferably only contacts the heat sink and the component(s). This ensures that the heat is not transferred via the housing, but is transferred in a directed manner along the heat-conducting profile, preferably by the shortest route, to the heat sink.

According to a preferred embodiment, the heat sink may have a coupling portion for coupling in a heat-conductive manner with an external counter-coupling portion. That is, the heat sink is provided and configured to transfer heat by heat conduction to the counter-coupling portion, which preferably acts as a heat removal component, in addition to heat dissipation via free/natural convection and heat radiation. Thus, all types of heat transport processes are utilized to dissipate heat in a particularly efficient but passive manner.

According to a further development of the preferred embodiment, the coupling portion may have a preferably planar contact surface, which is provided and configured to contact a surface of the counter-coupling portion, preferably directly, in particular with a surface-to-surface contact, in a heat-conducting manner. The surface-to-surface contact and the resulting contact surface can increase the transferable heat output.

According to a preferred embodiment, the cooling ribs may be oriented vertically, preferably in the position of use of the device. A vertical orientation favors gravity-induced natural/free convection.

In other words, the heat sink may have both a surface structure optimized in areas for heat convection and/or heat radiation, in the form of the cooling ribs, and a surface structure optimized in areas for heat conduction, in the form of the planar contact surface.

According to a preferred embodiment, the coupling portion may be arranged between the cooling ribs. This has the advantage that the natural convection caused by the cooling ribs can be used to circulate a flow around the coupling portion and the counter-coupling portion that can be received or is received therein (in the coupling portion), so that the coupling portion or counter-coupling portion also contributes to heat dissipation by convection. Thus, a particularly efficient system can be provided.

According to a preferred embodiment, the device may have a fixing portion for attaching the device to an external holding device, such as a stand clamp of a stand. This has the advantage that the device can be fixed in space and/or can be moved in space with the holding device. According to a further development of the preferred embodiment, the fixing portion may be formed by the coupling portion of the heat sink, and the external counter-coupling portion may be formed by the holding device. This means that the coupling portion simultaneously serves to fix the device. This has the advantage that the coupling portion has to be in contact with the holding device for fixing, so that the function of heat dissipation is integrally solved. A further advantage is that the coupling portion is covered by the holding device when in the fixed state and thus cannot be contacted unintentionally with the hand. Since the device is usually fixed via a metallic stand clamp or directly via a metallic stand, the heat-conducting contacting by the holding device with good heat conduction properties is possible without modifying the present system.

According to a further development of the preferred embodiment, the fixing portion may have a rail which is provided and configured to fix the device to the holding device in a form-fitting manner, in particular without tools. In this way, simple fixing can be ensured. In particular, an insertion direction of the fixing portion guided by the rail on the holding device may preferably correspond to an orientation of the cooling ribs and/or to a vertical direction. This has the advantage that the fixing of the device does not counteract free convection, for example by preventing air from flowing around the fixing portion.

In accordance with a further development of the preferred embodiment, the heat sink, in particular the coupling portion, may be arranged on a rear side of the housing (as seen in the position of use of the device). This reduces the risk of manual contact with the (hot) coupling portion. Alternatively or additionally, the heat sink may have a protection against contact covering the coupling portion and insulating it from the outside. This prevents burning due to unintentional contact. The protection against contact may have an insertion slot for the holding device so that fixing to the holding device is ensured.

According to a preferred embodiment, the housing may be substantially fluid-tight. This has the advantage that entering of undesirable media can be prevented. Preferably, the housing may be configured without ventilation openings. This means that the housing does not have any ventilation slots, ventilation openings or the like through which fluids can enter the interior of the housing from the outside.

According to a preferred embodiment, the heat sink may be made from a material having a heat conductivity greater than 10 W/mK, preferably greater than 50 W/mK, more preferably greater than 100 W/mK. Preferably, the heat sink may be made from a metal, in particular aluminum or copper. Alternatively, the heat sink may be made from a ceramic material, in particular from an engineering ceramic, such as aluminum oxide or aluminum nitride. This gives the heat sink good heat conduction properties.

According to a preferred embodiment, the heat sink may have a surface that has an emissivity greater than 0.8. Alternatively or additionally, the surface of the heat sink may be anodized. This has the advantage that the heat sink has good heat radiation properties.

The object is also solved by a system having a holding device and a described device. The heat sink of the device is connectable or connected to the holding device in a heat-conducting manner. Thereby the heat sink and the holding device serve as a radiator of the device, in particular of the component which is heat-generating at least during use of the device. An radiator is understood in particular to mean a body that emits heat predominantly by heat radiation (and/or also by convection). That is, a radiator is understood to be the opposite of a body that gives off heat predominantly by conduction. As a result, the heat sink itself emits heat to the environment via convection and/or heat radiation on the one hand and via heat conduction to the holding device on the other hand, which in turn emits heat to the environment via convection and/or heat radiation due to the significantly larger external surface area.

According to a preferred embodiment, the holding device may be made from a material having a thermal conductivity greater than 10 W/mK, preferably greater than 50 W/mK, more preferably greater than 100 W/mK. Preferably, the holding device may be made from a metal, in particular aluminum or copper. Alternatively, the holding device may be made from a ceramic material, in particular from an engineering ceramic, such as aluminum oxide or aluminum nitride. This gives the holding device good heat conduction properties.

In other words, the present disclosure relates to a device for the administration of medical fluid, in particular an infusion pump, such as a syringe pump or a hose pump, with fanless, passive cooling of the device electronics ((electronic) components). In this case, the heat generated by the electronic components is dissipated with the aid of heat-conducting profiles to a passive heat sink (attached to the outside of a housing of the device). The heat sink can preferably be attached to a rear side of the device. Furthermore, the heat sink may have an adaptation (holder function) for a stand clamp. This means that the heat sink may simultaneously have/configure an adapter which is adapted to hold the device on a stand and which is further optimized to transfer heat to the stand in this way via heat conduction and thus to increase the cooling capacity. In addition, a surface structure of the heat sink may be optimized for the cooling process/for heat convection. Such heat sinks are already known from other technical fields and are used, for example, in computers and combustion engines to dissipate heat from electrical energy to the environment. In medical technology, however, in particular in the field of infusion pumps, the use of heat sinks has not been known so far. In addition, the heat-generating electronic components of the device may preferably be arranged close together and may be thermally connected to a heat-conducting profile/sheet. The heat-conducting profile/sheet is thermally connected to the external heat sink so that the heat is dissipated to the environment via natural convection and heat radiation. In this way, the temperature can be kept within the permissible range for all components, while at the same time ensuring good cleanability of all areas accessible to fluids. In addition, the cooling system can thus function fail-safely and without consuming electrical energy.

BRIEF DESCRIPTION OF THE DRAWING FIGURES

DETAILED DESCRIPTION

A preferred embodiment of the present disclosure is described below based on the accompanying figures.

Figures 1, 2:
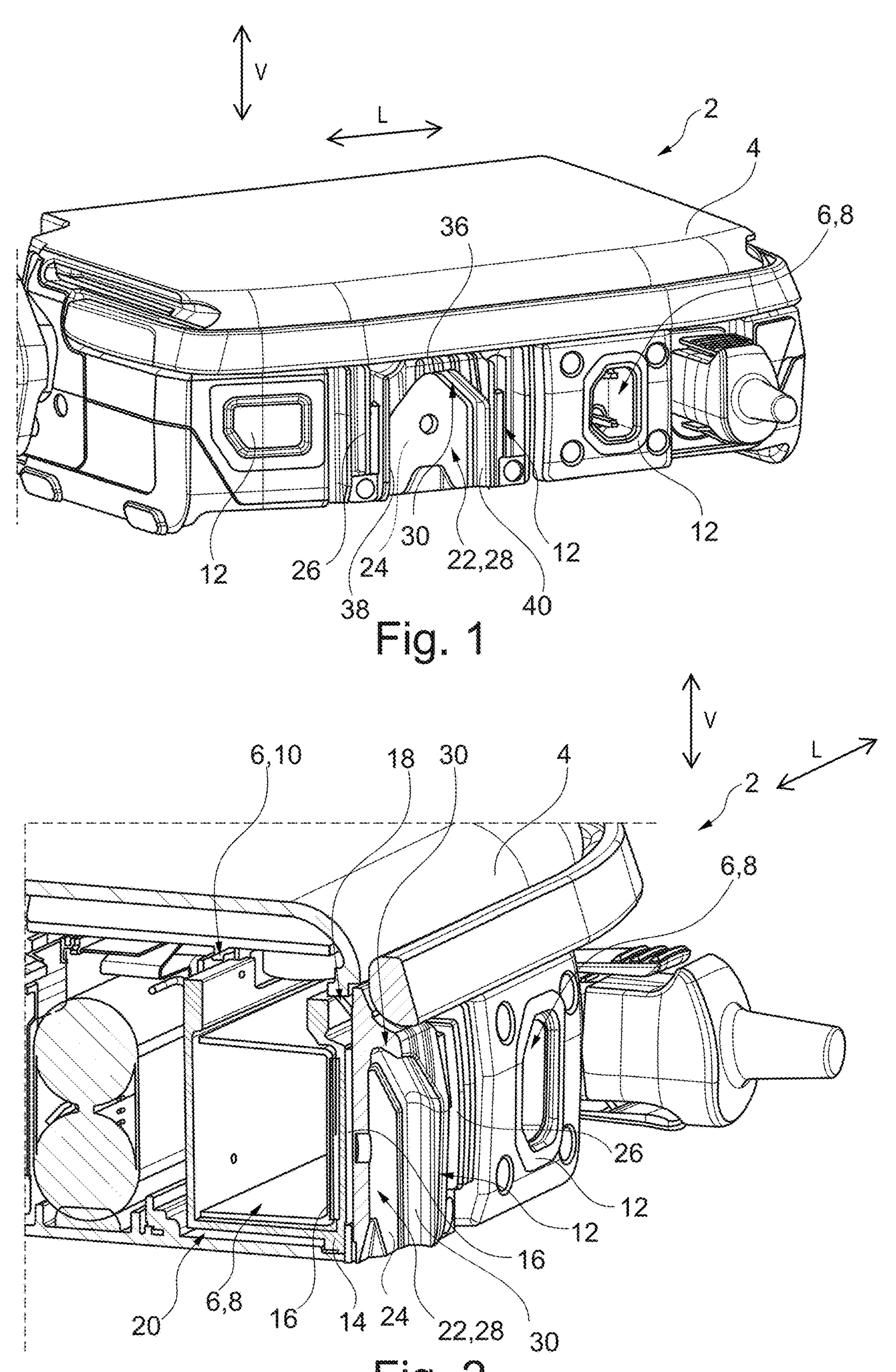
FIG. 1 is a perspective view of a device for administering medical fluids according to the present disclosure.
FIG. 2 is a perspective sectional view of the device.

FIGS. 1 and 2 show a device 2 for administering medical fluid according to the present disclosure. In particular, the device 2 is configured as an infusion pump, for example as a syringe pump or a hose pump. The device 2 has a housing 4 and at least one, in particular when the device is in use, heat-generating component 6, i.e. a component to be cooled. The component 6 is arranged inside the housing 4.

In the embodiment shown, the device 2 has two components 6 to be cooled. A power adaptor 8 for power supply is a heat-generating component 6 (cf. FIG. 2). A radio module 10 for signal transmission in the form of a WLAN-/WIFI-module is a heat-generating component 6 (cf. FIG. 2). Alternatively, the component 6 could also be formed by an accumulator for power supply, another radio module such as a Bluetooth module, a drive for conveying the fluid, a display unit for displaying operation-relevant data and/or a control device for controlling the device 2, even if this is not shown.

The device 2 has a passive heat sink 12. The heat sink 12 is attached/arranged on an outer side of the housing 4. The heat sink 12 is thermally connected, in particular in a heat-conducting manner, to the component 6 (or components 6). Thus, heat is transported by heat conduction from the interior of the housing 4 to the heat sink 12 on the outside, where it is released into the environment.

Preferably, the heat sink 12 may be made from a material whose heat conductivity is greater than 10 W/mK, preferably greater than 50 W/mK, more preferably greater than 100 W/mK. Preferably, the heat sink may be made from a metal, in particular aluminum or copper. Furthermore, the heat sink 12 may have a surface that has an emissivity greater than 0.8. Alternatively or additionally, the surface of the heat sink 12 may be anodized.

Preferably, the device 2 may have a heat-conducting profile 14 arranged inside the housing 4. The heat-conducting profile 14 is configured, for example, as a heat-conducting sheet or the like. The heat-conducting profile 14 may be thermally connected, preferably directly, i.e. with mechanical contact, to the component 6 (or components 6). The heat-conducting profile 14 may be thermally connected, preferably directly, i.e. with mechanical contact, to the heat sink 12. In particular, the heat-conducting profile 14 may be connected to the component 6 and/or the heat sink 12 in a surface-to-surface manner. Preferably, the heat-conducting profile may be made from a material whose heat conductivity is greater than 10 W/mK, preferably greater than 50 W/mK, further preferably greater than 100 W/mK. In particular, the heat-conducting profile 14 may be made from a metal, for example aluminum or copper.

Preferably, the heat sink 12 may have a contact surface that abuts (against) a contact surface of the heat-conducting profile 14. Alternatively, the contact surface of the heat sink 12 may be connected to the contact surface of the heat-conducting profile 14 via a thermal layer 16, such as a thermal paste (cf. FIG. 2). The contact surface of the heat sink 12 and/or the contact surface of the heat-conducting profile 14 are/is preferably configured to be planar. The heat sink may, for example, be arranged in such a way that it reaches through a recess 18 in the housing 4 in order to contact the heat-conducting profile 14 (cf. FIG. 2).

For example, the heat-conducting profile 14 may thermally connect multiple heat-generating components 6, in the illustrated embodiment the power adaptor 8 and the radio module 10, to the heat sink 12. Preferably, the multiple components 6, in the illustrated embodiment the power adaptor 8 and the radio module 10, are arranged adjacent to each other.

In addition, the heat-conducting profile 14 may be arranged at a distance from the housing 4. This means that a gap 20 is configured between an inner side of the housing 4 and the heat-conducting profile 14 (cf. FIG. 2) in order to prevent heat transfer via the housing 4.

According to a preferred embodiment, the heat sink 12 may include a coupling portion 22 for coupling in a heat-conducting manner with an external counter-coupling portion (not shown). Thus, the heat sink 12 can—in addition to heat dissipation via free/natural convection and heat radiation—transfer heat to the counter-coupling portion via heat conduction. Preferably, the coupling portion 22 may have a contact surface 24 which is provided and configured to contact a surface of the counter-coupling portion in a heat-conducting manner, preferably directly, in particular by surface-to-surface contacting. The contact surface 24 and/or the surface is/are preferably configured to be planar.

According to a preferred embodiment, the heat sink 12 may include cooling ribs 26, in particular to increase the surface area of the heat sink 12. For example, the cooling ribs 26 may be oriented vertically (i.e., in a vertical direction V) in the use position of the device.

In other words, the heat sink 12 may have both a surface structure optimized in areas for heat convection and/or heat radiation, in the form of the cooling ribs 26, and a surface structure optimized in areas for heat conduction, in the form of the planar contact surface 24. Preferably, the coupling portion 22 may be arranged between the cooling ribs 26 in a lateral direction L.

The device 2 may have a fixing portion 28 for attaching the device 2 to an external holding device (not shown). For example, the holding device may be configured as a stand or a stand clamp of a stand. Preferably, the fixing portion 28 may be formed by the coupling portion 22 of the heat sink 12. In other words, the coupling portion 22 simultaneously functions to fix the device 2. Thus, the holding device can serve as a counter-coupling portion. Thus, the contact between the fixing portion 28 and holding device can be used as a heat-conducting contact for transferring heat. For example, the fixing portion 28 may include a rail 30 that extends perpendicularly away from to the planar contact surface 24 along a top side 36 of the planar contact surface in the vertical direction V and along opposite lateral sides 38, 40 of the planar contact surface 24 in the lateral direction L, to define an inverted U-shaped wall that is provided and configured to form-fittingly fix the device 2 to the holding device, in particular without the use of tools. In particular, an insertion direction of the fixing portion 28 guided by the rail 30 on the holding device may preferably correspond to an orientation of the cooling ribs 26 and/or the vertical direction V.

Furthermore, complementary latching elements may be provided on the coupling portion 22 of the heat sink 12 and on the counter-coupling portion of the holding device to prevent unintentional detachment of the device 2 from the holding device.

According to the preferred embodiment, the heat sink 12, in particular the coupling portion 22, may be arranged on a rear side (as seen in the use position of the device) of the housing 4. Preferably, the heat sink 12 may have a protection against contact (not shown) covering the coupling portion 22 and insulating it from the outside. The protection against contact may have a slot for insertion for the holding device, so that fixing to the holding device is ensured.

Preferably, the housing 4 may be substantially fluid-tight, in particular it may be configured without ventilation openings. This means that the housing 4 has no ventilation slots, ventilation openings or the like through which fluids can enter the interior of the housing 4 from the outside.

Figure 3:
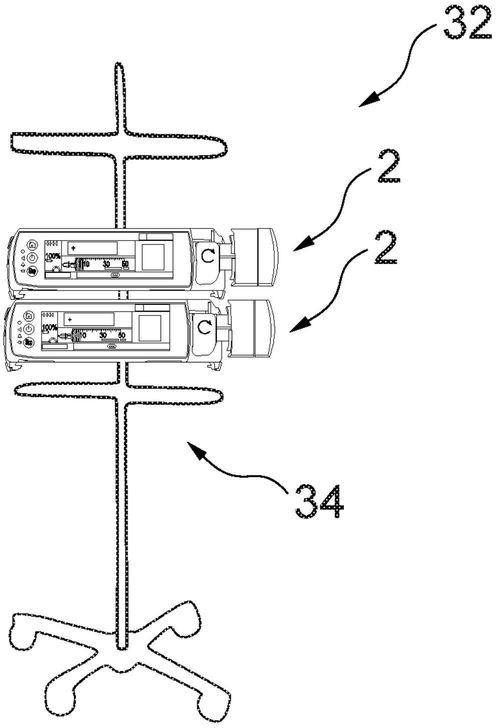
FIG. 3 is a schematic representation of a system comprising a holding device and the device.

The disclosure also relates to a system 32 comprising a holding device 34, such as a stand, and the described device 2. The system 32 is shown schematically in FIG. 3. The holding device 34 thus serves as the external holding device described above or, respectively, as the counter-coupling portion. Thereby, the heat sink 12 of the device 2 is connectable or connected in a heat-conducting manner to the holding device 34. Thereby, the heat sink 12 and the holding device 34 serve as a radiator of the device 2, in particular of the heat-generating component 6 at least during use of the device 2. Preferably, the holding device 34 may comprise a holding adapter which connects the heat sink 12 and the holding device 34 in a heat-conducting manner. In particular, the holding adapter may be inserted into the heat sink 12, for example via the rail 30. This enables form-fitting attachment of the device 2 to the holding device 34.

Preferably, the holding device 34 may be made from a material having a heat conductivity greater than 10 W/mK, preferably greater than 50 W/mK, more preferably greater than 100 W/mK. Preferably, the holding device 34 may be made from a metal, in particular aluminum or copper.

The invention claimed is:

1. A device for administering medical fluid, the device comprising:

a housing;

a component which is heat-generating at least when the device is in use and which is arranged inside the housing; and a heat sink that is passive, the heat sink being mounted on an outer side of the housing and connected to the component, the heat sink comprising:

cooling ribs extending in a vertical direction, and a coupling portion comprising:

a planar contact surface extending in the vertical direction, at a location in a lateral direction between at least two of the cooling ribs, and a rail extending perpendicularly away from the planar contact surface along a top of the planar contact surface in the vertical direction and along opposite lateral sides of the planar contact surface in a lateral direction, to define an inverted U-shaped wall.

2. The device according to claim 1, wherein a heat-conducting profile is arranged within the housing, the heat-conducting profile being thermally connected to the component and to the heat sink.

3. The device according to claim 2, wherein the heat-conducting profile is directly thermally connected to the component and/or the heat sink.

4. The device according to claim 1, wherein at least a portion of the rail extending perpendicularly away from to the planar contact surface along the top of the planar contact surface in the vertical direction comprises an undercut.

5. The device according to claim 4, wherein the heat sink serves as a radiator of the component which is heat-generating at least during use of the device.

6. The device according to claim 1, wherein the rail defines an insertion direction extending in the vertical direction.

7. The device according to claim 1, wherein the heat sink is arranged on a rear side of the housing, and/or the heat sink has a protection against contact covering the coupling portion and insulating the coupling portion from outside the housing.

8. The device according to claim 1, wherein the housing is substantially fluid-tight.

9. The device according to claim 1, wherein the heat sink is made from a material having a heat conductivity greater than 10 W/mK and/or a surface of the heat sink has an emissivity of greater than 0.8 and/or the surface of the heat sink is anodized.

10. The device according to claim 1, wherein the heat sink is connected to the component in a heat-conducting manner.

11. The device according to claim 1, wherein the coupling portion is arranged on a rear side of the housing.

12. The device according to claim 1, wherein the housing is configured without ventilation openings.

13. The device according to claim 1, wherein the heat sink is made from a metal.

14. The device according to claim 13, wherein the metal comprises aluminum or copper.

* * * * *